United States Patent [19]

Cope

[11] Patent Number: 5,123,914
[45] Date of Patent: Jun. 23, 1992

[54] VISCERAL ANCHOR FOR VISCERAL WALL MOBILIZATION

[75] Inventor: Constantin Cope, Elkins Park, Pa.

[73] Assignee: Cook Incorporated, Bloomington, Ind.

[21] Appl. No.: 864,340

[22] Filed: May 19, 1986

[51] Int. Cl.⁵ .............................................. A61B 17/00
[52] U.S. Cl. .................................. 606/232; 606/108; 606/215
[58] Field of Search .................................... 604/51-53; 128/334, 335, 339; 606/108, 144, 215, 220, 232

[56] References Cited

U.S. PATENT DOCUMENTS

| | | | |
|---|---|---|---|
| 3,521,640 | 7/1970 | Carey et al. | 128/334 R |
| 4,006,747 | 2/1977 | Kronenthal et al. | 128/335 |
| 4,077,412 | 3/1978 | Moossun | 604/51 |
| 4,235,238 | 11/1980 | Ogiu et al. | 128/334 R |
| 4,669,473 | 6/1987 | Richards et al. | 128/335 X |
| 4,705,040 | 11/1987 | Mueller et al. | 604/51 X |

Primary Examiner—C. Fred Rosenbaum
Assistant Examiner—Corrine Maglione
Attorney, Agent, or Firm—Woodard, Emhardt, Nauaghton, Moriarty & McNett

[57] ABSTRACT

A visceral anchor and method for visceral wall mobilization is disclosed. The visceral anchor includes an elongated cross bar to which a suture is attached at a location substantially in the center of the cross bar. The cross bar further includes a helical spring sheath which jackets a rigid rod, the sheath extending beyond the ends of the rod to form flexible ends. An alternative embodiment includes a second suture attached to one of the ends of the cross bar. The sutures are used for orienting the anchor during insertion into and removal from a hollow viscus. The method of visceral wall mobilization includes providing a tract through the skin into a hollow intra-abdominal viscus and inserting the anchor into the viscus lumen. The sutures extend through the tract and the unattached ends remain on the outside of the body. The center suture is pulled to orient the anchor for mobilization of the visceral wall. The end suture is pulled to orient the anchor for removal.

5 Claims, 3 Drawing Sheets

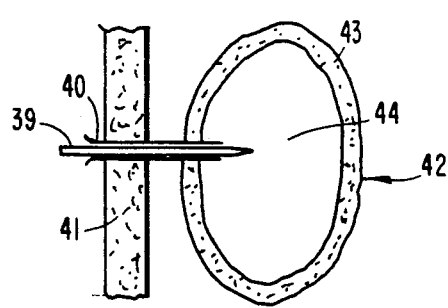
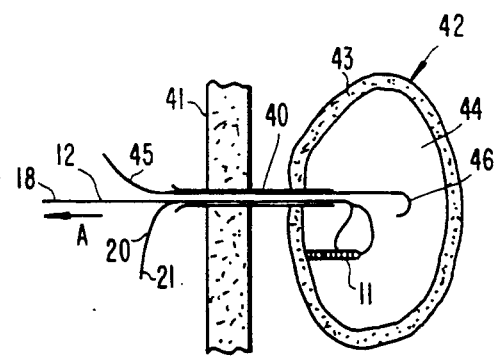
Fig.3     Fig.4
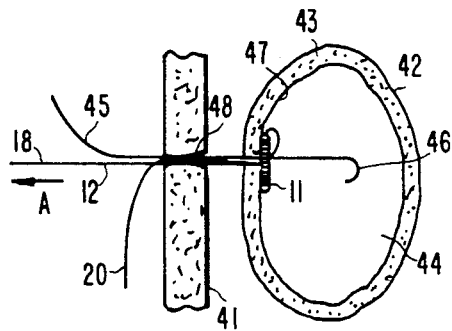
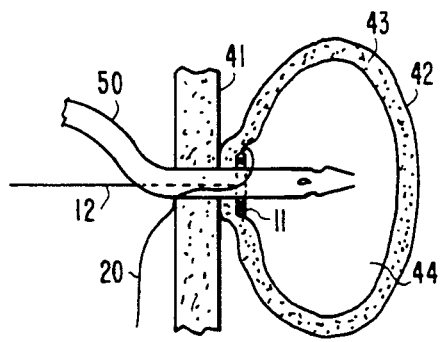
Fig.5     Fig.6
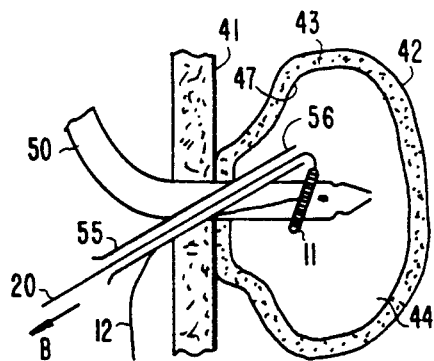
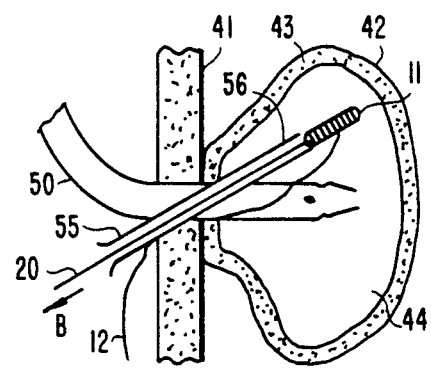
Fig.7     Fig.8

VISCERAL ANCHOR FOR VISCERAL WALL MOBILIZATION

BACKGROUND OF THE INVENTION

1. Field of the Invention

The present invention relates generally to the field of surgical methods and devices for establishing drains in intra-abdominal viscera.

2. Description of the Related Art

The insertion of a drain tube into the stomach, gall bladder and other intra-abdominal viscera carries an inherent risk of spillage of gastric juices, bile or infected fluids into the peritoneal cavity if the viscus becomes invaginated during tract dilation, or the wire guide becomes coiled within the peritoneal cavity and the drain cannot be reinserted. Therefore, one feature of this invention is to provide a visceral anchor which atraumatically mobilizes and internally tamponades the wall of the stomach, bowel, gall bladder and/or superficial abscesses against the abdominal or chest wall before inserting a larger retention loop or other drain.

Several and various devices and methods have been proposed for the purpose of facilitating the insertion of drains in intra-abdominal viscera. A stomach catheter placement system is disclosed in U.S. Pat. No. 3,961,632, issued to Moossun on Jun. 8, 1976. The Moossun system provides mobilization of the stomach wall using a magnetic nasogastric intubation device. Once the stomach wall is brought in proximity with the abdominal wall, a Foley type catheter is inserted through the abdominal wall into the stomach. The stomach wall is retained by an inflatable annulus on the catheter and an external locking disc. A method and apparatus for urinary drainage is disclosed in U.S. Pat. No. 3,598,124, issued to Anderson on Aug. 10, 1971. Anderson uses a Foley type catheter for retaining a drain in the bladder.

Several retractable mechanical devices for establishing, retaining, and removing percutaneous transport tubes are known in the related art. Examples include the devices disclosed in U.S. Pat. No. 4,393,873, issued to Nawash on Jul. 19, 1983; U.S. Pat. No. 3,039,468, issued to Price on Jun. 19, 1962; and U.S. Pat. No. 3,835,863, issued to Goldberg on Sep. 17, 1974. In Nawash, inadvertent removal of a transparent tube placed in the stomach is retarded by a resilient tip that assumes an outwardly bulged configuration upon the dissolving of a retention binding. Price discloses a trocar having retractable fingers. The fingers engage the stomach wall and a slidable clamp engages outer hide or skin in order to draw the stomach wall and the skin together around the cannula. The Goldberg device is a T-shaped drainage tube which is surgically implanted into a duct. Because of the flexibility of the cross tube, the arms of the cross tube fold to a substantially parallel position when the tube is withdrawn through the opening in the duct.

The use of guide wire in surgical methods of inserting catheters into vascular systems is described in U.S. Pat. No. 4,534,363, issued to Gold on Apr. 26, 1984. The Gold patent discloses an improved coating for angiographic guide wire and a method of manufacturing the guide wire.

As relates particularly to the present invention, there has not been provided heretofore a simple device and percutaneous method for atraumatically mobilizing and internally tamponading the wall of an intra-abdominal viscus against the abdominal or chest wall.

SUMMARY OF THE INVENTION

One embodiment of the present invention is a method of visceral wall mobilization utilizing a visceral anchor. The visceral anchor of this embodiment includes a biocompatible elongated cross bar and a flexible biocompatible suture attached at one of its ends near the center of the cross bar. A first step is providing a tract or passage from outside of the body through the skin and viscus wall to the viscus lumen. A further step is inserting the visceral anchor through the tract and into the viscus lumen. During insertion, the elongated cross bar is aligned along the longitudinal axis of the tract. The suture is left extending through the tract with the unattached end remaining on the outside of the body. A further is pulling the suture until the cross bar is aligned perpendicularly to the longitudinal axis of the tract and the cross bar engages the visceral wall. Further pulling of the suture will mobilize the visceral wall.

Another embodiment of the present invention is a method of visceral wall mobilization utilizing a retrievable visceral anchor. The retrievable visceral anchor of this embodiment includes a biocompatible elongated cross bar, one flexible biocompatible suture attached at one of its end near the center of the cross bar, and a second flexible biocompatible suture attached at one of its ends to one end of the cross bar. A first step of the method is providing a tract from outside of the body through the skin and viscus wall to the viscus lumen. The tract has a longitudinal axis extending from outside the body to the viscus lumen. A further step is inserting the visceral anchor through the tract and into the viscus lumen. During insertion, the cross bar is aligned along the longitudinal axis of the tract. The sutures are left extending through the tract with their unattached ends remaining on the ouside of the body. Another step is pulling the suture attached to the center of the cross bar until the cross bar is aligned perpendicularly to the longitudinal axis of the tract and the cross bar engages the visceral wall. Further pulling of the first suture will mobilize the visceral wall. Still another step is retrieving the visceral anchor by slackening the first suture so that the anchor is released from engagement with the visceral wall. The suture attached to the end of the cross bar is then pulled until the cross bar is aligned along the longitudinal axis of the tract and pulled through the tract.

Another embodiment of the present invention is a visceral anchor for insertion into a viscus lumen through the wall of a hollow viscus. The visceral anchor of this embodiment includes a biocompatible elongated cross bar and a flexible biocompatible suture attached at one of its ends near the center of the cross bar.

It is an object of the present invention to provide a visceral anchor and method of insertion for percutaneous insertion into a hollow viscus.

Relation objects and advantages of the present invention will be apparent from the following description.

BRIEF DESCRIPTION OF THE DRAWINGS

FIG. 3 is a schematic representation of a step in one embodiment of the method of visceral wall mobilization of the present invention.

FIG. 4 is a schematic representation of a further step of the method of FIG. 3, particularly showing the visceral anchor after insertion into a hollow viscus.

FIG. 5 is a schematic representative according to the method of FIG. 3, particularly showing the anchor positioned in perpendicular relation to the longitudinal axis of the tract and engaged with the visceral wall.

FIG. 6 is a schematic representation according to the method of FIG. 3, particularly showing the visceral wall retracted against the abdominal wall, and a drain tube inserted into the viscus lumen.

FIG. 7 is a schematic representation according to one embodiment of an anchor removal step of the method of the present invention, particularly showing the visceral anchor released from engagement with the visceral wall and the end suture extending through a cannula.

FIG. 8 is a schematic representation according to the anchor removal step of FIG. 7, paticularly showing the visceral anchor aligned along the longitudinal axis of the cannula prior to being removed with the cannula.

DESCRIPTION OF THE PREFERRED EMBODIMENT

Figure 1:
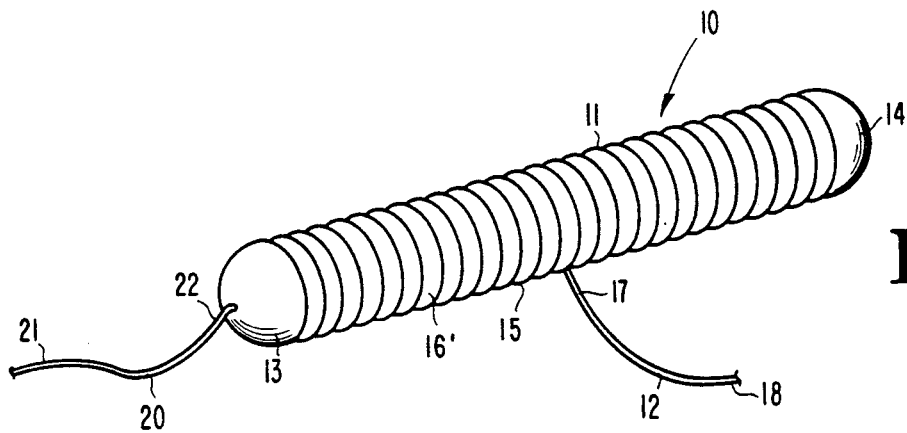
FIG. 1 is an enlarged perspective view of a visceral anchor according to a typically embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown visceral anchor 10 according to a preferred embodiment of the present invention. In the embodiment shown in FIG. 1, the visceral anchor 10 includes cross bar 11 and suture 12. The cross bar 11 is elongated and cylindrically shaped, and includes a center portion 15 interposed between the ends 13 and 14. The suture 12 includes an attached end 17 and an unattached end 18. Attached end 17 is attached to cross bar 11 at a location substantially in the center thereof. The anchor 10 further includes a suture 20, having unattached end 21 and an attached end 22 attached to the end 13 of the cross bar 11. Sutures 12 and 20 are typically constructed of common suture material. For example, in the preferred embodiment, 4-0 TEVDEK suture material is used. Preferably the sutures 12 and 20 are approximately 40 centimeters in length.

Figure 2:
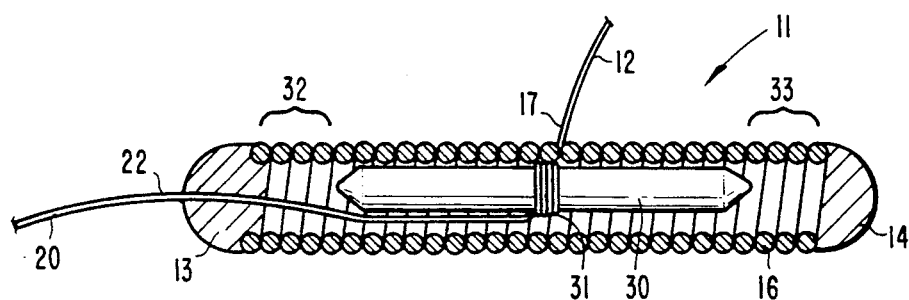
FIG. 2 is an enlarged fragmentary cross-sectional view of the visceral anchor of FIG. 1.

The internal construction of cross bar 11 is shown in FIG. 2. The center portion 15 of cross bar 11 includes a rigid rod 30 jacketed by a helical spring sheath 16. In the preferred embodiment, sheath 16 is standard stainless steel surgical wire guide material having an approximate outside diameter of 0.87 millimeters. Rod 30 may be a stainless steel cannula or rod. In the preferred embodiment, rod 30 is approximately 10 millimeters in length. Sheath 16 extends beyond the ends of rod 30 to form flexible end portions 32 and 33. It is desirable to provide flexible end portions so that anchor 10 may atraumatically engage the internal walls of intra-abdominal viscera. In the embodiment shown in FIG. 2, sutures 12 and 20 extend into the hollow of sheath 16 and are interconnected around rod 30 at location 31. The sutures 12 and 20 may constitute a single suture for ease of maufacture.

The ends 13 and 14 of cross bar 11 are rounded and extend beyond the ends of helical spring sheath 16. The ends 13 and 14 may be formed of any suitable biocompatible material capable of bonding to the sheath 16. For example, epoxy or a bead of metal welded to sheath 16 may be used. In the preferred embodiment, epoxy is provided to form and integrally bond ends 13 and 14 to sheath 16. The attached end 22 of the suture 20 is encased within end 13 to fasten suture 20 to cross bar 11. The suture 20 is thus secured yet passes through the epoxy material to be secured also at location 31, as previously described.

The method of visceral wall mobilization utilizing the visceral anchor is illustrated in FIGS. 3 through 7. Referring to FIG. 3, in the preferred embodiment of the method, a tract or passageway is established from outside of the body through the skin and viscus wall to the viscus lumen by a needle puncture. In the preferred embodiment, a 15 centimeter long 22 gauge needle 39, over which a cannula or 16 gauge plastic sheath 40 is mounted, is used for puncture. Once the distended viscus lumen is localized with the protruding needle, the outer cannula or sheath is advanced over it, and the sheath left in place, defining the tract. With the sheath in place, the needle is removed. FIG. 3 shows plastic sheath 40 defining the tract extending from outside the body through abdominal wall 41 and visceral wall 43, into viscus lumen 44 of viscus 42.

FIG. 4 shows a further step of the method wherein the cross bar 11 is inserted through the tract defined by sheath 40 into viscus lumen 44. Cross bar 11 is aligned along the longitudinal axis of the tract during insertion, with sutures 12 and 20 trailing through sheath 40 with their unattached ends 18 and 21 remaining on the outside of the body. Cross bar 11 is pushed through sheath 40 with a 0.038 inch "J" tipped wire guide 45. FIG. 4 shows cross bar 11 within viscus lumen 44, after having been pushed through sheath 40 by the wire guide 45.

Next the suture 12 is pulled by grasping it with the sheath 40, causing the cross bar 11 to be positioned in perpendicular relation to the longitudinal axis of the tract and causing the cross bar 11 to engage the internal wall of the hollow viscus. The pulling force is exerted on suture 12 in the general direction indicated by arrow A. The sheath 40 is removed over the sutures 12 and 20, providing the condition illustrated in FIG. 5. FIG. 5 illustrates cross bar 11 aligned perpendicularly to needle tract 48 and engaged with internal visceral wall 47. The length of cross bar 11 is greater than the diameter of needle tract 48, and therefore cross bar 11 engages internal visceral wall 47. Further pull or traction is exerted on the suture 12 until the visceral wall is moved into close approximation to the abdominal wall. With the visceral wall firmly retracted against the parietal wall, there is little chance of intraperitoneal leakage. Tension on suture 12 is maintained by securing the suture 12 to skin using a standard surgical needle.

The wire guide 45 is now be used to further dilate the needle tract 48 by pushing one or more increasingly larger dilators over the wire guide and into the viscus lumen. Such dilators are commercially available and therefore have not been shown herein. Drain tube 50 may then be inserted with impunity to provide communication between viscus lumen 44 and the outside of the body. FIG. 6 illustrates inserted drain tube 50, while cross bar 11 retains visceral wall 43 against abdominal wall 41. The loose suture 20 is taped to drain tube 50.

A few days later when the drain tract has been established, the visceral anchor 10 may no longer be necessary and can be easily removed. Referring now more particularly to FIGS. 7 and 8, the suture 12 is cut, thus releasing the tension on the cross bar 11. A cannula 55 which may be, for example a 5 French cannula, is employed to remove visceral anchor 10. The cannula 55 is threaded over suture 20 as shown in FIG. 7 and inserted alongside the drain tube 50 back into the viscus lumen 44. Once distal end 56 of cannula 55 is inside viscus lumen 44, a gentle force in the general direction of arrow B may be applied on the suture 20. The cross bar 11 will realign itself along the longitudinal axis of cannula 55 as shown in FIG. 8 and can then be easily withdrawn along with cannula 55. The end 13 of cross bar 11 is held in contact with distal end 56 of the cannula by tension on suture 20, thereby maintaining coaxial alignment during withdrawal of cannula 55 and cross bar 11. The suture 12 will trail the cross bar 11 as the cross bar and cannula are withdrawn.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

Figure 9:
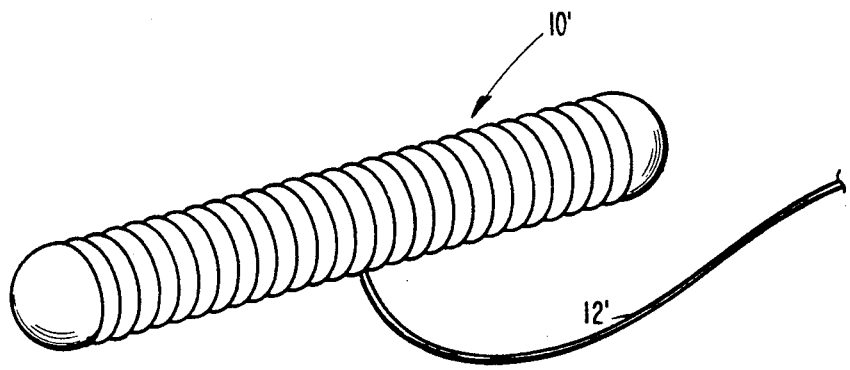
FIG. 9 is a perspective view of an alternative embodiment of the visceral anchor of the present invention.
Figure 10:
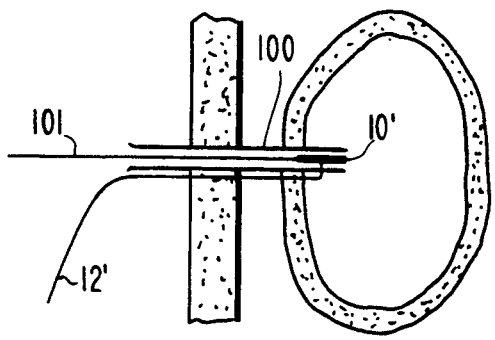
FIG. 10 is a schematic representation of a step in an alternative embodiment of the method of visceral wall mobilization of the present invention.
Figure 10A:
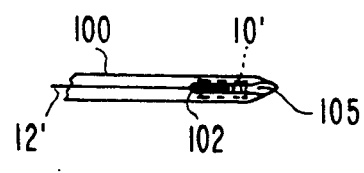
FIG. 10A is a view of the needle of FIG. 10 looking at the needle at a 90° angle as compared to FIG. 10.

For example, FIG. 9 shows an alternative embodiment of the visceral anchor 10' which is identical to the embodiment of FIGS. 1 and 2 with the exception that the suture 20 is not present. The single suture embodiment of FIG. 9 is used in an application where the anchor 10' is not retrieved, unlike the above described retrievable anchor 10. Such a visceral anchor 10' is mounted near the distal end of the inserting needle as shown in FIG. 10 and is placed during initial puncture. In FIG. 10 the needle 100 has in its hollow interior the anchor 10' and a wire guide 101 which is used to push the anchor 10' out of the needle when penetration of hte viscus is achieved. Correct needle position is confirmed by injecting radiopaque dye or aspirating viscus fluid through proximal needle slot 105 before ejecting anchor 10'. The length of the slot in the needle is slightly longer than the anchor so as to provide an "injection port" 102 from which the dye is ejected. The needle and wire guide are then withdrawn and the viscus is firmly retracted against the abdominal wall as above described.

What is claimed is:

1. A visceral anchor comprising:

a biocompatible elongated cross bar having opposite ends;
a first flexible biocompatible suture having a first attached end and a second unattached end, the first attached end being attached to said cross bar at a location substantially in the center of said cross bar; and
the opposite ends of said cross bar being flexible, and there being interposed between said flexible opposite ends a relatively rigid center portion, the first attached end being attached to the center portion, whereby said flexible opposite ends are adapted for atraumatic engagement with body tissue being anchored.

2. A visceral anchor comprising:

a biocompatible elongated cross bar having opposite ends;
a first flexible biocompatible suture having a first attached end and a second unattached end, the first attached end being attached to said cross bar at a location substantially in the center of said cross bar;
the opposite ends of said cross bar being flexible, and there being interposed between said flexible opposite, ends a relatively rigid center portion, the first, attached end being attached to the center portion, whereby said flexible opposite ends are adapted for atraumatic engagement with body tissue being anchored; and
a second flexible biocompatible suture having a third attached end and a fourth unattached end, the third attached end being attached to one of said opposite ends of said cross bar.

3. A visceral anchor comprising:

a biocompatible elongated cross bar having opposite ends;
a first flexible biocompatible suture having a first attached end and a second unattached end, the first attached end being attached to said cross bar at a location substantially in the center of said cross bar;
the opposite ends of said cross bar being flexible, there being interposed between the flexible ends a rigid center portion, the first attached end being attached to the center portion;
a second flexible biocompatible suture having a third attached end and a fourth unattached end, the third attached end being attached to one of the opposite ends of said cross bar; and
said cross bar comprises a biocompatible rigid rod and a biocompatible helical spring sheath, the rod being jacketed by the sheath, the sheath extending beyond both ends of the rod to form said flexible ends.

4. The visceral anchor of claim 3 in which:

the cross bar opposite ends include epoxy material at their outermost points, the epoxy being bonded to the helical spring sheath.

5. The visceral anchor of claim 4 in which:

said first suture and said second suture are of unitary construction, the first attached end and third attached end being connected beneath the sheath.

* * * * *

UNITED STATES PATENT AND TRADEMARK OFFICE
CERTIFICATE OF CORRECTION

PATENT NO. : 5,123,914
DATED : June 23, 1992
INVENTOR(S) : Constantin Cope

It is certified that error appears in the above-indentified patent and that said Letters Patent is hereby corrected as shown below:

In column 2, at line 18, insert --step-- after "further".

In column 2, at line 60, change "Relation" to --Related--.

In column 2, at line 65, change "typically" to --typical--.

In column 4, at line 10, change "maufacture" to --manufacture--.

In column 5, at line 51, change "hte" to --the--.

In column 6, at line 24, delete the "," after the word "site".

Signed and Sealed this

Thirty-first Day of August, 1993

Attest:

Attesting Officer

BRUCE LEHMAN

*Commissioner of Patents and Trademarks*